United States Patent [19]

Biedermann et al.

[11] Patent Number: 5,716,356
[45] Date of Patent: Feb. 10, 1998

[54] ANCHORING MEMBER AND ADJUSTMENT TOOL THEREFOR

[76] Inventors: Lutz Biedermann, Am Schafersteig 8, VS-Villingen, Germany, 78048; Jurgen Harms, Vogesenstr. 60, Waldbronn, Germany, 76337

[21] Appl. No.: 617,858

[22] PCT Filed: Mar. 1, 1995

[86] PCT No.: PCT/EP95/00742

§ 371 Date: May 17, 1996

§ 102(e) Date: May 17, 1996

[87] PCT Pub. No.: WO96/02198

PCT Pub. Date: Feb. 1, 1996

[30] Foreign Application Priority Data

Jul. 18, 1994 [DE] Germany .................. 44 25 357.5

[51] Int. Cl.⁶ ............................................ A61B 17/70
[52] U.S. Cl. ..................... 606/61; 606/60; 606/72; 606/73
[58] Field of Search ................... 606/60, 61, 65, 606/72, 73

[56] References Cited

U.S. PATENT DOCUMENTS

| | | | |
|---|---|---|---|
| 5,496,321 | 3/1996 | Puno et al. | 606/61 |
| 5,545,165 | 8/1996 | Biederam et al. | 606/73 |

FOREIGN PATENT DOCUMENTS

| | | |
|---|---|---|
| 0348272 | 12/1989 | European Pat. Off. . |
| 0 441729 | 8/1991 | European Pat. Off. . |
| 0487895 | 6/1992 | European Pat. Off. . |
| 2697428 | 5/1994 | France .................... 606/61 |
| 37 22590 | 12/1988 | Germany . |
| 42 34118 | 4/1994 | Germany . |
| 4307576 | 4/1994 | Germany . |
| 691 00953 | 6/1994 | Germany . |

*Primary Examiner*—Michael Buiz
*Assistant Examiner*—Daphna Shaz
*Attorney, Agent, or Firm*—George W. Neuner

[57] ABSTRACT

An anchoring member is provided with a shaft 2, 12 for anchoring in a bone and a head 3, 53 with a substantially U-shaped cross-section for connection with a rod 9, 59, the head having a base 5, 55 connected with the shaft 2, 12 and two free legs 6, 7; 56, 57 forming a channel for receiving the rod 9, 59. The two legs have an internal screw thread 8, 58 and an external screw thread 8', 58'. A nut member 11, 61 comprises an internal thread which embraces the outside of the legs and cooperates with the external screw thread and a locking member 10 has a thread cooperating with the internal screw thread of the legs. The anchoring member further comprises a spring member 19, 79 acting onto the rod 9, 59 to be received in order to, on the one hand, obtain a rigid connection between the anchoring member and the rod and, on the other hand, to allow an easy manipulation for precisely adjusting the position between the anchoring member and the rod before finally locking the position.

29 Claims, 7 Drawing Sheets

ANCHORING MEMBER AND ADJUSTMENT TOOL THEREFOR

The invention relates to an anchoring member according to the preamble of claim 1 and an adjustment tool therefor.

Such an anchoring member is known from document DE 42 34 118 A. This anchoring member is perfectly suited for connection with a rod to be carried. For readjusting this anchoring member the nut member and the fixing member must be temporarily loosened to allow relative displacement between the anchoring member and the rod. Document DE 37 22 590 C discloses a positioning device for stabilizing segments of the spinal column whereby the rod is formed as a threaded rod and the rod is locked to the anchoring member by means of two nuts engaging the outside of the anchoring member and being adjustable on the threaded rod. For readjusting the position of the rod relative to the anchoring member the nuts are correspondingly rotated on the threaded rod.

It is the object of the invention to provide an anchoring member of the initially described kind and an adjustment tool therefor which, on the one hand, allows to obtain a good connection between the anchoring member and the rod and, on the other hand, provides for an easy adjustment manipulation.

This object is achieved by the anchoring member as defined in claim 1 and by the adjustment tool as defined in claims 28 and 39, resp..

Further embodiments of the invention are defined in the dependent claims.

Further features and advantages of the invention will be apparent from the description of an embodiment with reference to the Figures. In the Figures.

Figure 1:
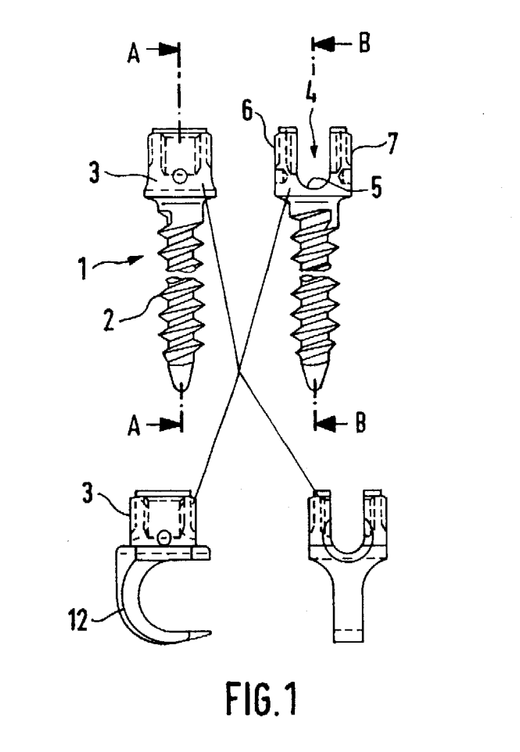
FIG. 1 is a lateral view of an anchoring member and a side view perpendicularly thereto.

The anchoring member shown in FIG. 1 comprises a screw 1 for insertion into the spinal column, the screw having a threaded shaft 2 and a head 3. The head comprises a U-shaped recess 4 which is symmetric with respect to the center axis of the threaded shaft 2 and has a base 5 at the side of the threaded shaft. The lateral wall of the head defining the U-shaped recess 4 is formed by lateral free legs 6, 7. A bore having an internal screw thread 8 is provided within the channel formed by the U-shaped recess 4 and formed coaxially with the center axis of the threaded shaft 2. The head 3 itself is cylindrical and has an external screw thread 8'.

In order to allow the anchoring of a rod 9 by means of this screw a locking member 10 formed as a screw is provided. The locking member 10 has an external thread cooperating with the internal screw thread 8 for screwing into the U-shaped recess 4. The locking member 10 further comprises a coaxial recess for engagement of a hexagon socket screw key. Moreover, there is a member embracing the outside of the two U-shaped legs 6, 7, the member being formed as a swivel nut 11 having a thread cooperating with the external screw thread 8'. Preferably, the direction of rotation of the internal screw thread 8 and the associated locking member 10 is opposite to the direction of rotation of the outer screw thread 8' and of the swivel nut. As shown for example in FIG. 3 the base 5 of the U-shaped recess has a radius which is larger than the radius of the rod 9 to be placed therein by such an amount only that the rod can be easily inserted into the U-shaped recess and removed therefrom, resp. The internal screw thread 8 and the external screw thread 8' both extend downwardly, i.e. in direction to the base 5, by such an extent that the projection onto the axis of symmetry has a distance from the base 5 which is smaller than the diameter of the rod 9 to be placed therein.

As shown in FIG. 1 the anchoring member can be provided with a hook 12 in place of the threaded shaft 2. The hook as well serves for connection with a member of the spinal column, whereby the hook is placed in a bow of the vertebra.

Figure 2:
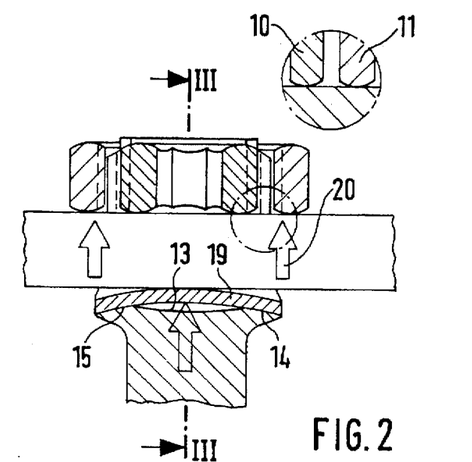
FIG. 2 shows a portion of the anchoring member according to a first embodiment with a rod placed therein, in sectional representation.
Figure 3:
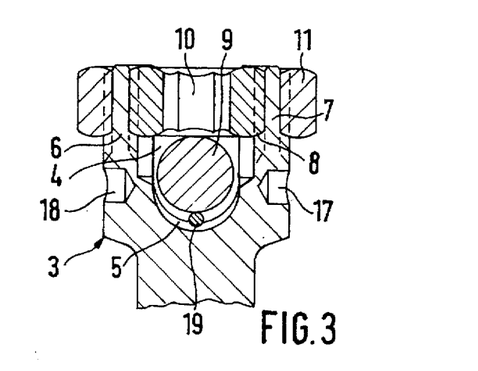
FIG. 3 is a sectional view along line III—III in FIG. 2.

In the first embodiment shown in the FIGS. 2 and 3 the base of the respective U-shaped recess is curved. The curvature comprises a first inner concave portion 13 and two upwardly projecting cambered second portions 14, 15 arranged on both sides of the center axis of the screw symmetrically thereto. The respective apex of the second portions is spaced from the center axis of the screw by an amount which is substantially equal to the distance of the center between the radius of the inner thread 8 and the radius of the outer thread 8' from the axis of symmetry of the screw. As best shown in FIG. 3 the head 3 comprises two holes 17, 18 which are mutually offset by 180° and which are both offset from the U-shaped recess 4 by essentially 90°. The holes 17, 18 serve for engagement of a tool, for example gripping pliers.

As best shown in FIG. 2 a spring member 19 formed as a spring rod is recessed at the base 5 of the channel formed by the U-shaped recess 4. To this end the lateral projecting second portions of the base both have a groove for receiving the edge portion of the spring member 19. The spring member is fastened to one of the sides by laser spot welding.

As shown in FIG. 2 the convex curvature of the spring member 19 towards the open end of the channel is chosen to raise the rod 9 from the base to a position spaced from the projecting second portion if no additional force acts upon the rod.

In the above-described embodiment the spring member 19 is formed as a spring rod. The spring may be formed in a different manner. In particular, it can be a leaf spring which is inserted in a similar manner. It may also be a compression spring which is aligned along the axis of symmetry of the screw. When using a leaf spring or a spring rod, resp., the springs are preferably aligned to extend along the longitudinal center axis of the channel.

In operation the rod 9 is first placed into the channel formed by the recess 4. The swivel nut 11 is loosely screwed on so as to hold the rod 9 in a selected position thereof by exerting a slight binding force, but without already deforming the spring member 19. The locking member 10 is then screwed in to also frictionally engage the rod. By the clamping cooperation in particular of the swivel nut 11 and the spring member 19 the position of the rod 9 is fixed. A corresponding anchoring member is arranged in each segment of the spinal column and provisionally clamped to the rod 9 in a position selected by the operator.

In a following phase segment after segment is finely adjusted whereby the engagement position of each anchoring member at the rod relative to the longitudinal axis of the rod must be adjusted. To this end a pressure force acting in a direction opposite to the arrows 20 shown in FIG. 2 is exerted onto the rod 9 at both opposite sides of the rod adjacent to the swivel nut 11 at the corresponding anchoring member so that the rod is lifted off from the swivel nut 11 and from the locking member 10 and may be easily displaced in a direction parallel to the axis of the rod to a position corresponding to the precise adjustment. Thereafter the rod is released and clamped in the position shown in FIG. 2. This adjustment operation can be repeated as desired. Thereupon the swivel nut 11 is tightened so that the rod 9 presses the spring member 19 onto the base and the rod 9 is perfectly non-positively clamped between the swivel nut 11 and the base. The locking member 10 is then screwed in direction towards the rod until a desired locking force is obtained. In this manner the swivel nut 11 is clamped in position and can not loosen in future operation.

Figure 4:
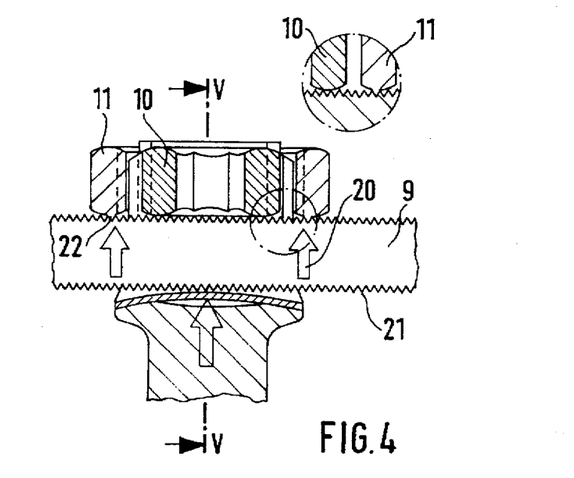
FIG. 4 is a sectional view of a second embodiment.
Figure 5:
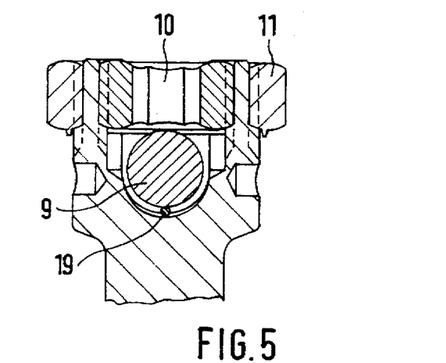
FIG. 5 is a sectional view along line V—V in FIG. 4.

The embodiment shown in the FIGS. 4 and 5 differs from the above-described embodiment by the following features:

The surface of the rod 9 is formed as a thread 21. Further, the edge of the swivel nut 11 facing the rod 9 comprises a projecting ring 22 best shown in FIG. 10. The dimensions of this ring are selected as function of the type of the thread 21 so that the ring engages the thread in a position screwed onto the rod, as shown in FIG. 4.

In operation of this second embodiment the swivel nut 11 and the locking member 10 are first rotated into the position shown in FIG. 4 wherein the relative position of anchoring member and rod is fixed by clamping and engagement of the ring 22 with the thread 21. For the following precise adjustment the rod 9 is pressed downwardly, as above described, in direction opposite to the arrows 20 and therefore opposite to the spring bias, whereby the engagement of the ring 22 with the thread, and between the swivel nut and the locking member on the one hand and the rod 9 on the other hand, is released. In this pressed-down position the rod is displaced according to the desired adjustment of the segment. When the new desired position is attained, the pressure force exerted onto the rod is released so that the locking position shown in FIG. 4 is again obtained. For final fixation first the swivel nut and then the locking member are again screwed in direction towards the base 5 until each of the two members exerts a desired clamping force onto the rod 9 and the swivel nut 11 is locked.

Figure 6:
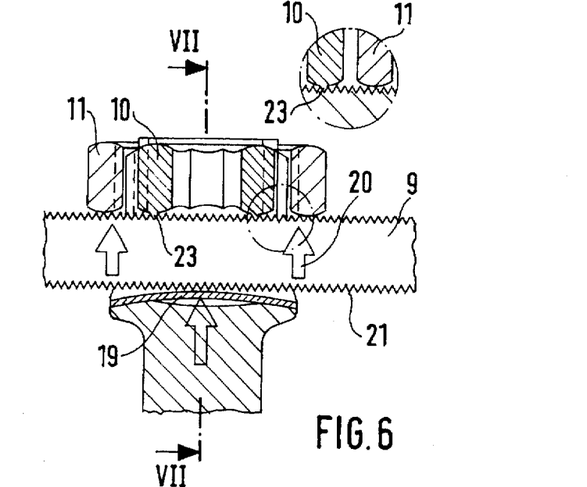
FIG. 6 is a sectional view of a third embodiment.
Figure 7:
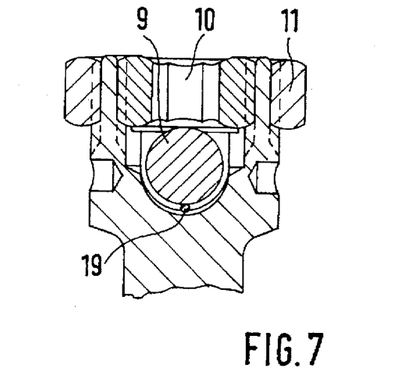
FIG. 7 is a sectional view along line VII—VII in FIG. 6.

The embodiment shown in FIGS. 6 and 7 differs from the above-described second embodiment in that the swivel nut is formed in the same manner as that of the first embodiment and the locking member 10 comprises a ring 23 corresponding to the ring 22, whereby the ring 23 upon contact of the locking member with the rod engages the thread and prevents an axial displacement of the rod 9 relative to the anchoring member in cooperation with the clamping force effected by the spring member 19. The precise adjustment and the final locking is made in the same manner as in the second embodiment.

Figures 8, 8A, 9:
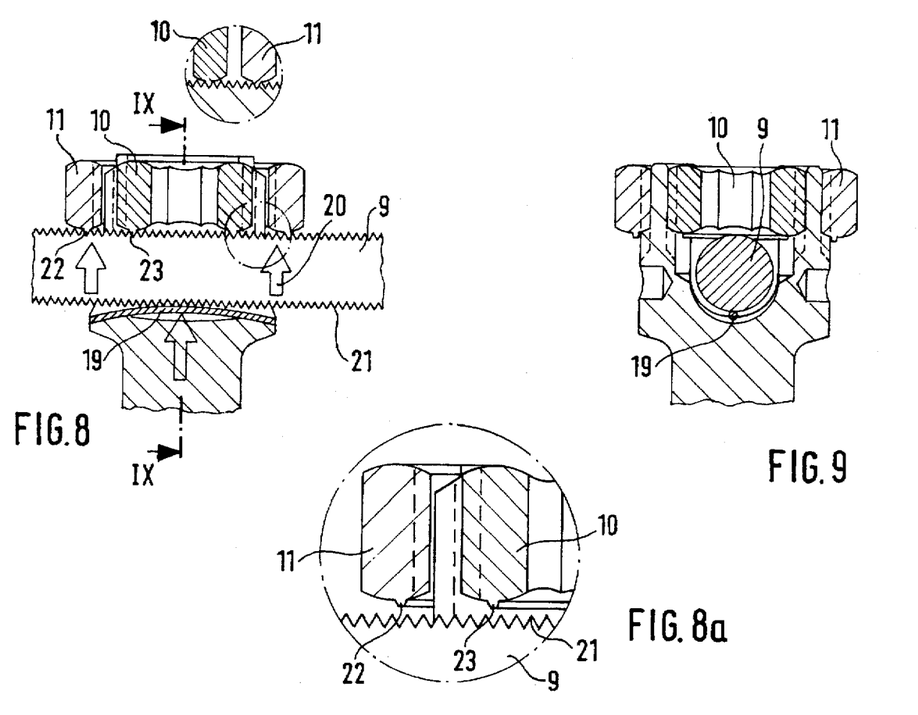
FIG. 8 is a sectional view of a further modified embodiment.
FIG. 8a shows a detail of FIG. 8 in enlarged representation.
FIG. 9 is a sectional view along line IX—IX in FIG. 8.
Figure 10:
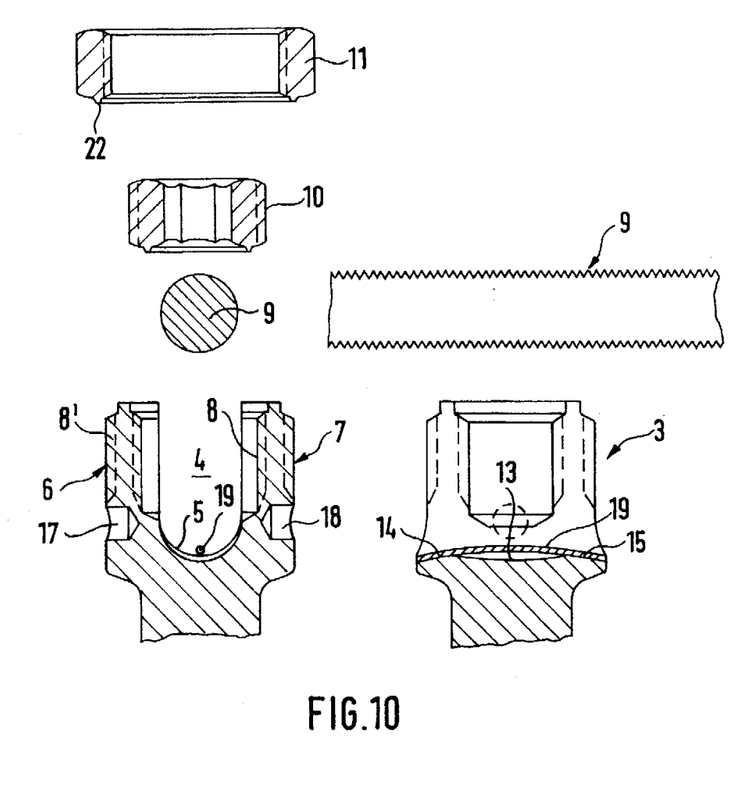
FIG. 10 is an exploded representation of the embodiment shown in FIG. 8.

The fourth embodiment shown in FIGS. 8 to 10 differs from the second and third embodiment, resp., in that the swivel nut comprises the ring 22, as in the second embodiment, and the locking member comprises the ring 23, as in the third embodiment. In operation the preliminary adjustment, the precise adjustment is made by pressing onto the rod 9 opposite to the direction of the arrows 20 and the subsequent final locking is made in the same manner as in the previous embodiments. In the clamping state effected by the spring force of the spring member 19 the two rings 22 and 23 engage the thread 21 and thus contribute in locking the rod against axial displacement relative to the anchoring member.

The further embodiment shown in the FIGS. 11 to 14 differs from the above-described embodiments in that the spring member, rather than being provided on the base of the recess 4 forming the channel, is arranged on the axially opposite side. The anchoring member formed as a screw 51 or a hook, resp., comprises a head 53 with a recess 54 forming a channel. The channel is defined by the base of the channel 55 and lateral legs 56, 57. In the same manner as before an internal screw thread 58 and an external screw thread 58' are provided. The channel serves to receive a rod 59 having the same shape as rod 9. A swivel nut 61 having the same construction as the swivel nut 11 of the first embodiment is provided.

Figures 13, 14:
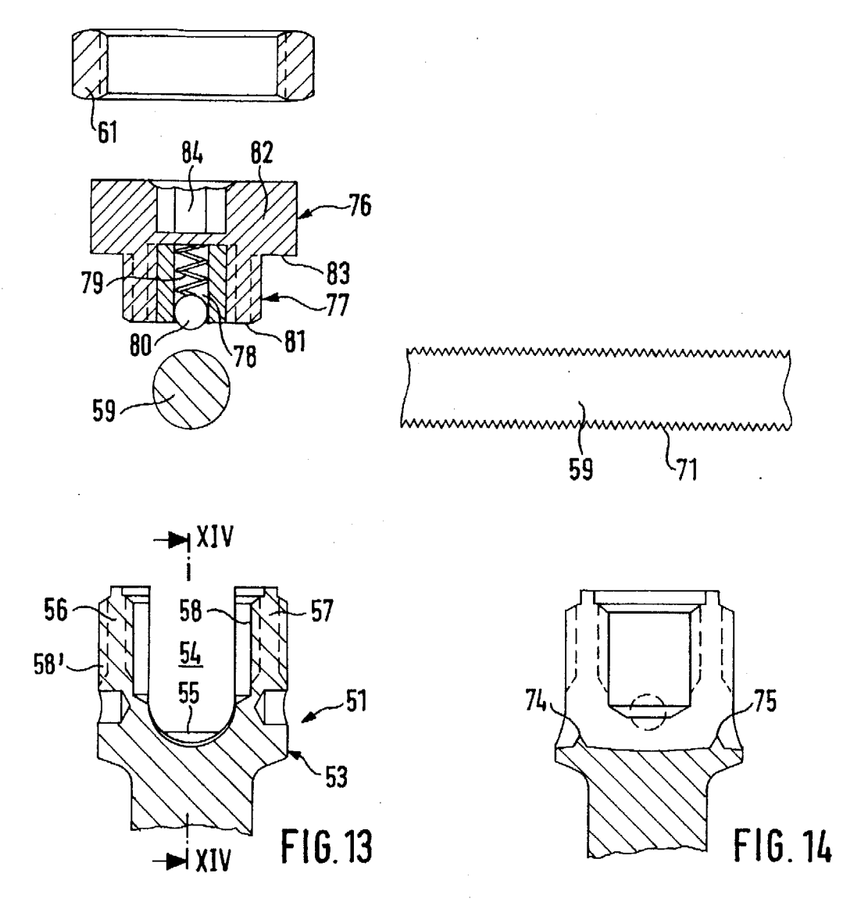
FIG. 13 is an exploded representation of the embodiment shown in FIGS. 11 and 12.
FIG. 14 is a partial sectional view of FIG. 13 along line XIV—XIV in FIG. 13.

Different from the previously described embodiments the base 55 of the channel best shown in FIG. 14 comprises a straight shape extending substantially perpendicular to the screw axis. Both lateral portions of the channel base have noses 74, 75 projecting upwardly in direction of the open side of the channel. Preferably, the noses are in the plane of symmetry of the channel. The shape of the noses is selected in dependence on the thread 71 of the rod 59 so that the noses may engage the thread when in contact with the rod 59. The two noses 74, 75 are each spaced from the center axis of the screw so that each nose is about centrally between the radius for the internal screw thread 58 and the radius for the external screw thread 58'.

An adjustment head 76 comprises a threaded portion 77 having an external thread which is designed to match the internal screw thread 58. A blind hole 78 receiving a compression spring 79 is coaxially provided within the side of the threaded portion 77 facing, in operation, the base of the channel. A ball member 80 is provided opposite to the base of the blind hole. The compression spring 79 is dimensioned to hold the ball member 80 in a position whereby the ball member projects beyond the front face 81 of the threaded portion by a predetermined amount, as shown in FIG. 13.

On the side opposite to the front face 81 the adjustment head comprises a cylinder portion 82 having a diameter which is larger than the diameter of the threaded portion so as to form a radially extending stop shoulder 83 on the side facing the threaded portion. The cylinder portion 82 has a coaxial hexagon bore 84 for insertion of a screwing tool on the side opposite to the threaded portion 77.

Figure 11:
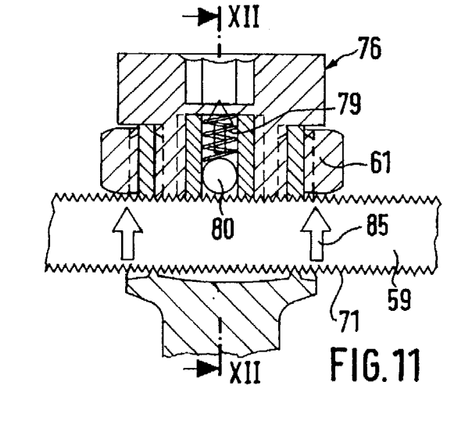
FIG. 11 is a sectional view of a further modified embodiment.
Figure 12:
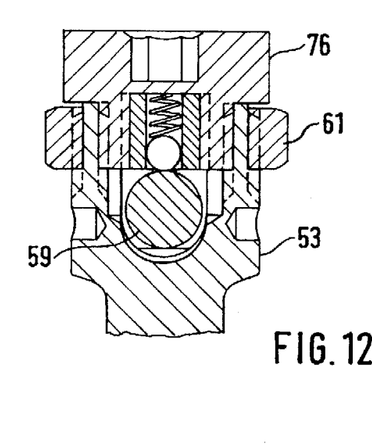
FIG. 12 is a sectional view along line XII—XII in FIG. 11.

In operation the rod 59 is first placed into the channel in the manner shown in FIG. 11. The swivel nut 61 is loosely screwed on and then the adjustment head is screwed in up to its stop. The axial length of the threaded portion 77 is chosen in dependence on the length of the legs 56, 57 and of the diameter of the rod 59 so as to obtain, when screwing in the adjustment head up to its stop, a pressure force acting onto the rod 59 by cooperation of the compression spring 79 and the ball member 80, the pressure force causing an engagement of the rod 59 with the noses 74, 75 so that the rod 59 can not be displaced relative to the anchoring member. For carrying out the above-described precise adjustment the rod 59 is moved in direction of the arrows 85 towards the adjustment head by an amount which releases the engagement between the noses 74, 75 and the thread 71. When in this position the rod 59 can be laterally displaced relative to the anchoring member to a position corresponding to the precise adjustment. After displacement the rod is let go off whereby the bias of the compression spring 59 again causes an engagement of the noses 74, 75 with the thread 71 in the locking position shown in FIG. 11.

After precise adjustment the swivel nut 11 is rotated towards the channel base until a desired holding force acts onto the rod 59. Basically it is possible to leave the adjustment head as it is. However, the anchoring member is preferably formed to have, in addition to the adjustment head 76, a screw corresponding to the locking member 10 of the first embodiment. After adjustment the adjustment head is screwed out and replaced by a locking member 10 which is screwed in to such an extent that a desired holding force acts onto the rod 59 so as to cause in particular a clamping action between the swivel nut 61 and the legs 56, 57 which prevents loosening of the swivel nut. In the above-described embodiment the rod 9 or 59, resp., is formed either as a smooth rod or as a threaded rod. Other than the thread the rod may also have a surface comprising a cross thread or radially extending grooves. The rod 9 or 59 may also be formed as a rack on its side cooperating with the rings 22, 23 or with the noses 74, 75, resp.

Figure 15:
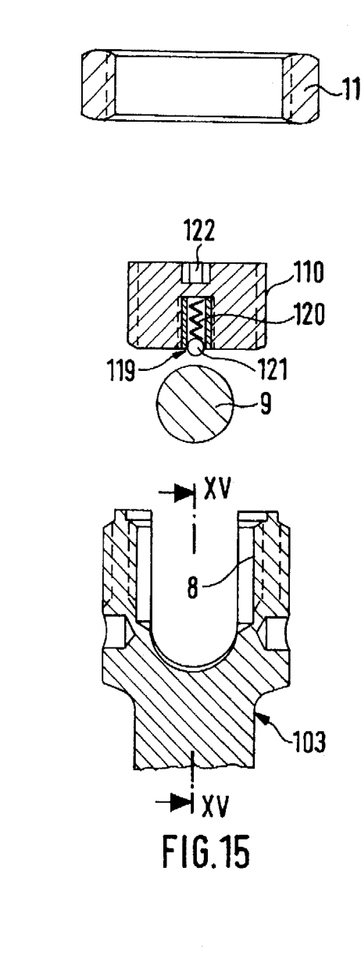
FIG. 15 is an exploded representation of a further embodiment.
Figure 15A:
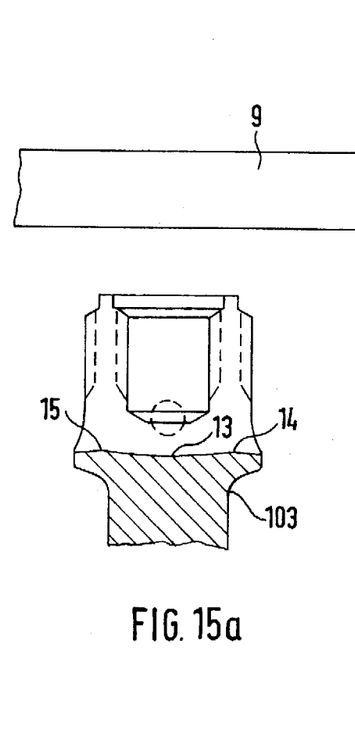
FIG. 15a is a sectional view along line XV—XV in FIG. 15.
Figure 16:
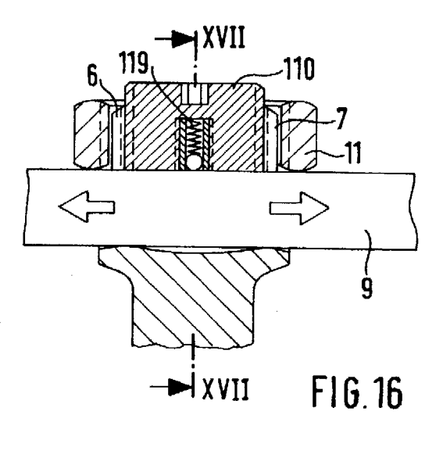
FIG. 16 shows the embodiment in assembled state.
Figure 17:
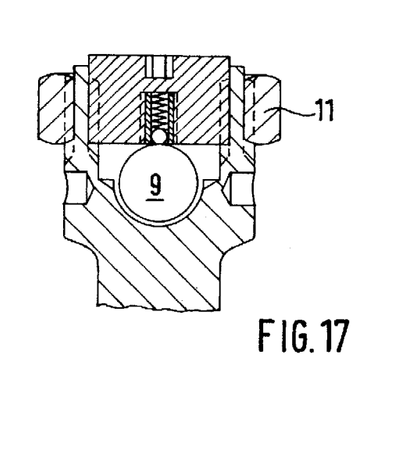
FIG. 17 is a sectional view along line XVII—XVII in FIG. 16.

The embodiment shown in FIGS. 15 to 17 comprises an anchoring member having a head 103 which corresponds to the head 3 of the first embodiment with the exception that the head 103 has no spring member. The rod 9 corresponds to that of the first embodiment, likewise the swivel nut 11. The locking is made by a locking member 110 which is formed as a cylinder member and has an outer size comprising a thread which matches with the internal screw thread of the head 3. The locking member 110 comprises a spring member 119 provided on its side facing the channel base. The spring member comprises a blind hole with a compression spring 120 therein which carries, on its free side, a ball member 121. The spring is dimensioned so as to hold the ball projecting by a predetermined amount beyond the adjacent front face of the locking member. On its opposite front face the locking member 110 has a coaxial hexagon bore 122 for receiving a screwing tool.

In operation the rod 9 is first placed into the channel. Thereupon the swivel nut 11 is screwed on so as to leave a play between the swivel nut 11 and the rod 9. The locking member 110 is then screwed in so as to leave a play between the rod and the front face of the locking member facing the rod 9, on the one hand, and to provide a contact between the ball of the spring member 119 and the rod 9, on the other hand, in a manner that the spring member 119 exerts a force onto the rod 9 which sufficiently clamps the rod 9 to prevent a displacement of the rod 9 relative to the anchoring member by the fact that the rod 9 rests on the projecting portions 14, 15 and the spring member 119 acts upon the opposite side of the rod.

For displacing the rod to obtain a precise adjustment the rod 9 is pulled into the one or other direction by exerting a pulling force which overcomes the clamping force, without relocating the locking member. After finishing the precise adjustment the swivel nut 11 is first tightened so as to obtain the desired holding force. Thereupon the locking member 110 is tightened by a predetermined amount so that a sufficient clamping effect is obtained between the legs 6 and 7 on the one hand and the swivel nut on the other hand and an unintentional loosening thereof is prevented.

Figure 19:
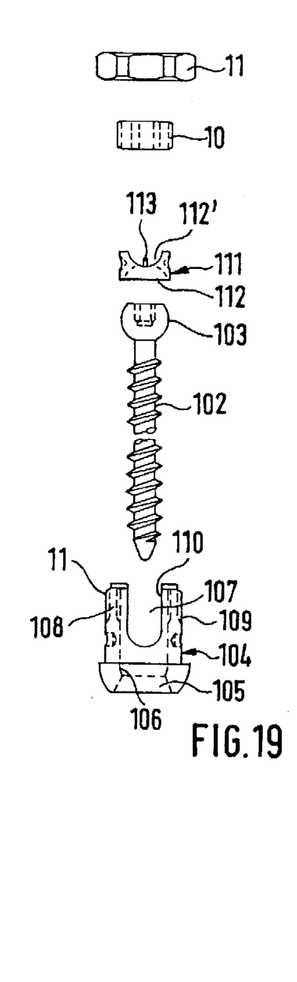
FIG. 19 is an exploded representation of this embodiment.
Figure 20:
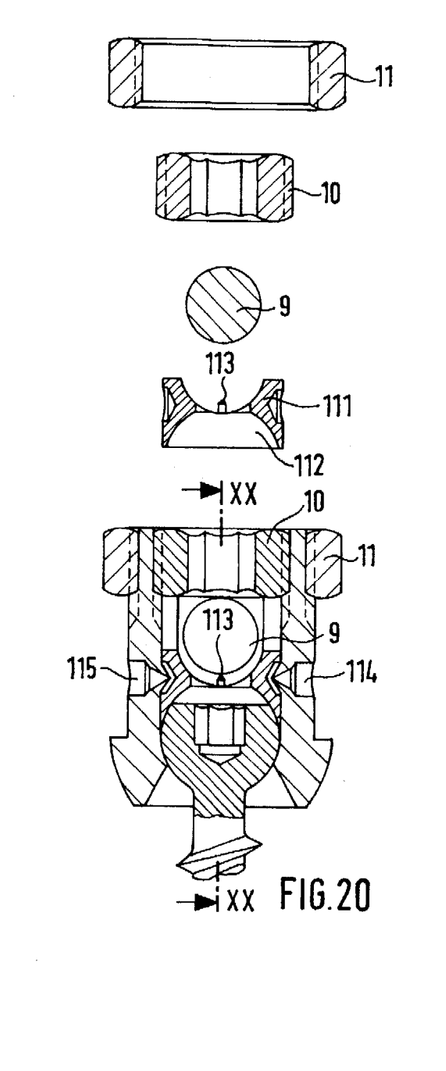
FIG. 20 is a detailed representation.
Figure 20A:
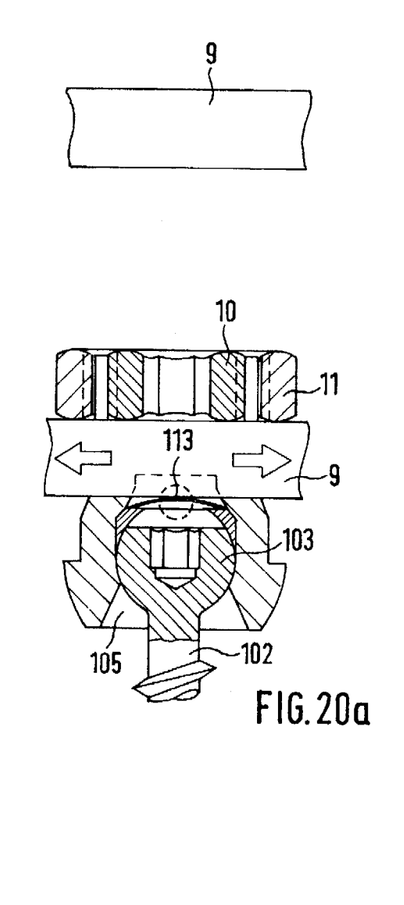
FIG. 20a is a sectional view along line XX—XX in FIG. 20.

The embodiment shown in the FIGS. 19 to 20a differs from the previous embodiments in particular in that the screw is formed as a so-called polyaxial screw whereby the head receiving the rod is hingedly connected to the associated threaded shaft. The same reference signs are used for those parts of this embodiment which correspond to the above-described embodiments.

Figure 18:
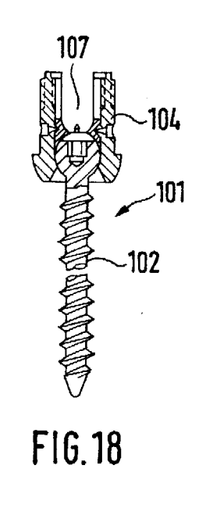
FIG. 18 is a sectional view of a further embodiment.

The screw 101 comprises a threaded shaft 102 and a head 103 having a spherical segment-shaped portion. Further, a cylindrical seat part 104 for receiving the head 103 has a first bore 105 at one end thereof for passing the threaded portion 102 therethrough. The bore is followed by an inner hollow spherical portion 106 for fitting the spherical head 103. A second bore 107 opening towards the side opposite to the first bore 105 is provided for introducing the threaded shaft part 102 together with the head 103. The cylinder portion has a U-shaped recess which is symmetric with respect to the center axis of the threaded shaft. As in the first embodiment the lateral walls of the head defining the U-shaped recess are formed by lateral free legs 108, 109. A bore having an internal screw thread 110 and being coaxial with the center axis of the threaded shaft is provided in the interior of the channel formed by the U-shaped recess. The head 104 has an external screw thread 111' on its outer side. A compression member 111 acting onto the head 103 is formed to have a spherical countersunk portion 112 on its side facing the head 103, the radius of the portion 112 being substantially equal to the radius of the spherical segment-shaped portion of the head 103. The outer diameter of the compression member is so as to allow a back and forth displacement of the compression member within the cylindrical recess. The surface of the compression member is formed to have a cylindrical recess 112 on its side opposite to the head 103, whereby the recess extends perpendicular to the screw axis. In a manner corresponding to the first embodiment a spring member 113 corresponding to the spring member 19 is provided on the base of this recess. In fabrication the parts 102, 103 and 111 are assembled as shown in FIG. 18. In order to provide for an exact positioning of the axis of the cylindrical recess 112 in the plane of symmetry of the U-shaped channel the position of the compression member 111 is fixed by crimping through bores 114, 115 when assembling, as best shown in FIG. 20.

Further, a locking member 10 and a swivel nut 11 are provided as in the first embodiment.

In operation the rod 9 is placed into the U-shaped channel of the preassembled anchoring member as shown in FIG. 18. The temporary locking, precise adjustment and final locking is then made in the same manner as in the first embodiment by using the locking member 10 and the swivel nut 11.

In the above-described embodiment the movable screw head has been described in connection with the previously described first embodiment. In place of the smooth rod 9 a rod having the structured surfaces corresponding to the above-described examples may be used. The locking member 10 and the swivel nut 11, resp., may comprise rings 22 or 23, resp., as in the above-described examples. Finally, an adjustment head corresponding to the adjustment head 76 may be used in place of the spring member 113 or a locking member 110 having a spring member may be used.

Figure 22:
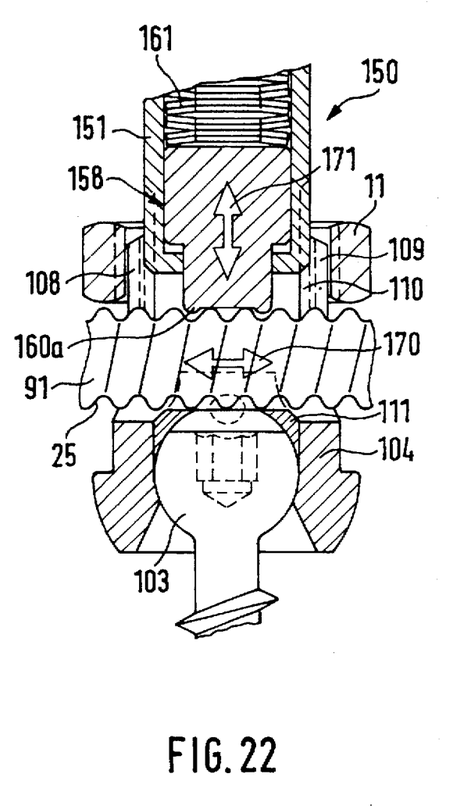
FIG. 22 is a sectional view of the anchoring member with the rod placed therein and with inserted adjustment tool.

The surface of a rod 91 may for example comprise a wavy thread or rounded thread 25, as shown in particular in FIG. 22.

Figure 21:
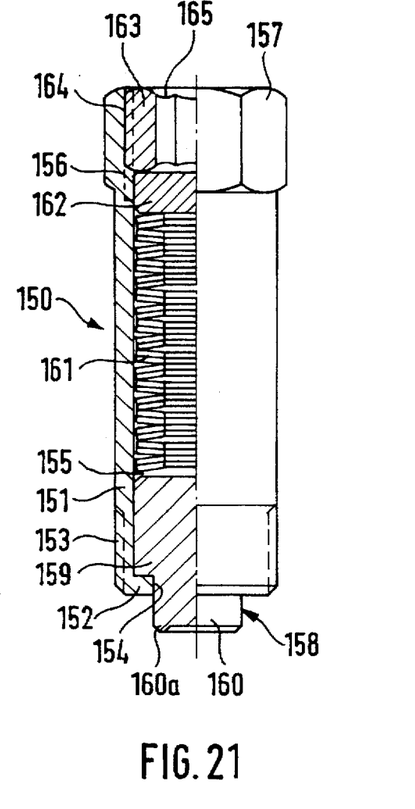
FIG. 21 is a partially sectional view of an adjustment tool.

An adjustment tool 150 shown in FIG. 21 is provided for adjusting the position of the seat part 104 relative to the rod and for locking the head 103 of the polyaxial screw within the seat part 104. The adjustment tool comprises a housing having a cylindrical jacket 151 and a face 152. The region of the jacket 151 adjacent to the face 152 has an external screw thread 153 corresponding to the internal screw thread 110 of the seat part 104. A circular aperture 154 is provided in face 152. A coaxial bore 155 having a diameter which is larger than the diameter of the aperture 154 is provided in the interior of the jacket adjacent to the aperture 154. The bore 155 extends to the end of the jacket 151 opposite to the face 152 so that the housing has an open end thereat. The jacket has an internal screw thread 156 at this end opposite to the face 152. The housing further comprises, at the region of the jacket having the internal screw thread 156, a portion 57 having a cross-section of hexagon shape in a plane perpendicular to the cylinder axis of the jacket 151 for engagement with a wrench.

The adjustment tool further comprises a pressure piece 158 seated within the jacket and having a first cylindrical portion 159 and an adjacent second cylindrical portion 160, whereby the outer diameter of the first cylindrical portion is slightly smaller than the diameter of the bore 155 and the outer diameter of the second cylindrical portion 160 is slightly smaller than the diameter of the aperture 154 so that the pressure piece 158 is displaceable in axial direction within the bore 155, with the second cylindrical portion 160 of the pressure piece 158 then projecting out of the aperture 154. The adjustment tool further comprises a compression spring disposed within the bore 155 and acting on the pressure piece 158, the compression spring being formed by stacked disk springs 161 having an outer diameter which is slightly smaller than the diameter of the bore 155. Moreover, a cylindrical pressure member 162 acting on the disk springs is provided within the bore at the side of the disk springs 161 opposite to the pressure piece 158. The outer diameter of the pressure member 162 is slightly smaller than the diameter of the bore 155 so that it may easily be displaced in axial direction within the bore. The pressure member 162 is pressed onto the disk springs 161 by means of a threaded screw 163 disposed within the bore 155 and acting on the pressure member. The threaded screw 163 comprises an external thread 164 screwed into the internal screw thread 156 of the jacket. The threaded screw 163 further comprises a central hexagon recess 165 for engagement of a hexagon socket screw key.

The second cylindrical portion 160 of the pressure piece 158 comprises an annular projection 160a provided on its face projecting from the aperture 154, whereby the annulus is formed by a coaxial circular recess formed within the face of the portion 160. The edges of the annular projection 160a are rounded. The diameter of the annular projection 160a corresponds to an integral multiple of the pitch of the rounded thread 25 of the rod 91 to be received and the height of the annular projection is smaller than the depth of the rounded thread 25 so that respective opposite regions of the annular projection 160a engage the convolutions of the rod 91.

In operation the positions of the individual anchoring members on the rod are precisely adjusted segment after segment.

To this end the swivel nut 11 is loosely screwed onto a preassembled anchoring member as shown in FIG. 22 having a rod 91 placed therein and thereafter the adjustment tool is screwed into the internal screw thread 110 of the legs until the rod 91 is pressed onto the compression member 111 resting on the screw head 103 by means of the pressure piece 158 which is preloaded by the disk springs 161. Thus, a movement of the screw head 103 relative to the seat part 104 is blocked. At the same time the annular projection 160a engages the convolutions of the round thread 25 of the rod 91 so that no displacement of the rod in direction of the arrows 170 shown in FIG. 22 parallel to the rod axis may occur without action of external forces. The preload of the pressure piece 158 can be suitably adjusted by compressing the disk springs 161 by means of the pressure member 62 through the threaded screw 163.

In order to precisely adjust the position of the seat part 104 relative to the rod 91 the rod 91 may thereafter be relocated by manual pushing or pulling, resp., in directions indicated by the arrows 170 in FIG. 22 parallel to the rod axis, whereby the adjustment tool acts as a ratchet. In the course of this the corresponding portions of the annular projection 160a of the pressure piece 158 disengage from the rounded thread 25 of the rod 91, whereby the pressure piece 158 is moved in a direction opposite to its preloading direction, as indicated by the arrow 171 in FIG. 22, until the annular projection 160a catches the next convolution of the thread and the pressure piece 158 is again in its preloaded position. The force necessary for adjusting the relative position of rod 91 and seat part 104 depends on the preload of the pressure piece 158.

It is the advantage of the adjustment tool that it allows a precise adjustment in steps corresponding to the pitch of the thread 25 of the rod 91. It is easy to carry out the precise adjustment, because the fact that the annular projection 160a catches the convolutions of the rounded thread can easily be acoustically perceived.

We claim:

1. Anchoring member comprising:

a shaft, a head having a substantially U-shaped cross-section with a base connected to said shaft and two free legs forming a channel for receiving a rod and having an internal screw thread and an external screw thread, a nut member embracing said legs and having an internal screw thread cooperating with said external screw thread of said legs, a locking member having a thread cooperating with said internal screw thread of said legs, and a spring member acting upon said rod.

2. The anchoring member of claim 1, wherein the spring member is located at said base of said channel.

3. The anchoring member of claim 1, wherein said shaft has a shaft axis and said spring member is preloaded in a direction parallel to said shaft axis.

4. The anchoring of claim 3, wherein said channel has an open end and said spring member is preloaded in a direction towards said open end.

5. The anchoring member of claim 1, wherein said channel has a plane of symmetry and said spring member is formed as a spring rod or leaf spring extending parallel to said plane of symmetry.

6. The anchoring member of claim 5, wherein said channel has an open end and said spring member is convex towards said open end of said channel.

7. The anchoring member of claim 6, wherein said channel has a channel edge and said spring member is welded to said channel edge.

8. The anchoring member of claim 1, further comprising a recess formed in said channel base and having a shape corresponding to said spring member for pressingly receiving said spring member within said recess.

9. The anchoring member of claim 1, further comprising a cambered portion formed at said base of said U-shaped cross-section, said cambered portion extending in a direction perpendicular to said U-shaped cross-section.

10. The anchoring member of claim 9, wherein said base comprises edges and said edges are formed to drop away towards said shaft in an outward direction.

11. The anchoring member of claim 9, wherein said cambered portion comprises a depressed center portion.

12. The anchoring member of claim 11, wherein said cambered portion comprises two projecting cambered regions spaced from a center of said base on opposite sides thereof.

13. The anchoring member of claim 12, wherein said spacing of said cambered region corresponds substantially to the center between a radius of said internal screw thread and a radius of said external screw thread.

14. The anchoring member of claim 10, wherein said spring member lies on said outwardly dropping edges.

15. The anchoring member of claim 1, further comprising a recess formed in said base of said channel, said recess being coaxial to said internal screw thread.

16. The anchoring member of claim 1, wherein said rod has a textured surface.

17. The anchoring member of claim 16, said textured surface comprises a thread, a cross-thread or grooves extending in peripheral direction of said rod.

18. The anchoring member of claim 16, wherein said textured surface comprises wavy helical convolutions.

19. The anchoring member of claim 16, said textured surface comprises a toothed portion extending parallel to the longitudinal axis of said rod on one side thereof.

20. The anchoring member of claim 16, wherein said nut member or said locking member comprises an engagement portion for engaging said textured surface, said engagement portion being formed on the side of said nut member or locking member facing said rod.

21. The anchoring member of claim 20, wherein said engagement portion is formed as a projecting edge.

22. The anchoring member of claim 16, wherein said nut member and said locking member comprises an engagement portion for engaging said textured surface, said engagement portion being formed on the side of said nut member and locking member facing said rod.

23. The anchoring member of claim 22, wherein said engagement portion is formed as a projecting edge.

24. The anchoring member of claim 1, wherein said channel has a channel base surface and an open end, and wherein said anchoring member further comprises at least one nose projecting from said channel base surface towards said open end.

25. The anchoring member of claim 24, wherein said locking member comprises a spring-biased member, said spring bias acting to urge said rod towards said channel base.

26. The anchoring member of claim 25, wherein said locking member comprises stop means for preventing said locking member from being further screwed in towards said channel base.

27. The anchoring member of claim 26, further comprising a screw member for finally locking said rod, said screw member being formed without said stop means.

28. The anchoring member of claim 1, wherein said shaft is formed as a threaded screw or as a bone hook.

29. The anchoring member of claim 1, wherein said head comprises rod receiving means for receiving said rod and said anchoring member further comprises a hinge to connect said rod receiving means with said shaft.

* * * * *